United States Patent

Igarashi et al.

[11] Patent Number: 4,552,695
[45] Date of Patent: Nov. 12, 1985

[54] PROCESS FOR PRODUCTION OF DILTIAZEM HYDROCHLORIDE

[75] Inventors: Kikuo Igarashi, Hyogo; Tsunetoshi Honma, Nara, both of Japan

[73] Assignee: Shionogi & Co., Ltd., Osaka, Japan

[21] Appl. No.: 600,405

[22] Filed: Apr. 16, 1984

[30] Foreign Application Priority Data

Apr. 21, 1983 [JP] Japan .................................. 58-71138
Apr. 21, 1983 [JP] Japan .................................. 58-71139
Apr. 21, 1983 [JP] Japan .................................. 58-71140

[51] Int. Cl.$^4$ ........................................... C07D 281/02
[52] U.S. Cl. .............................. 260/239.3 B; 549/548; 549/549; 549/555; 560/17
[58] Field of Search .................. 260/239.38 B

[56] References Cited

FOREIGN PATENT DOCUMENTS 57-136580 2/1981 Japan ............................. 260/239.3 B
57-136581 2/1981 Japan ............................. 260/239.3 B Primary Examiner—Robert T. Bond Attorney, Agent, or Firm—Wenderoth, Lind & Ponack

[57] ABSTRACT

New route to diltiazem hydrochloride of the formula:

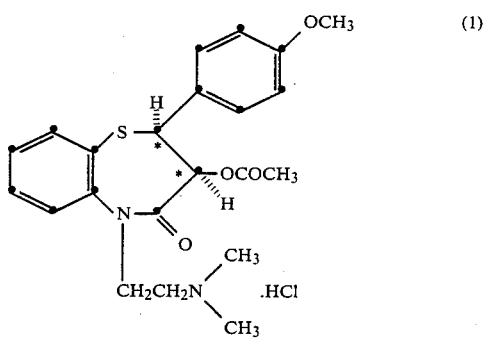

in which the starting cinnamyl alcohols are epoxidized by a special asymmetric synthesis followed by a series of stereospecific reactions; no optical resolution is required at any stage.

1 Claim, No Drawings

PROCESS FOR PRODUCTION OF DILTIAZEM HYDROCHLORIDE

BACKGROUND OF THE INVENTION (A) Field of the invention

The present invention relates to a new process for producing a calcium antagonist named as diltiazem hydrochloride. In particular, it relates to a stereospecific synthesis of the said compound having two asymmetric carbons.

(B) Description of the Prior Art

Diltiazem hydrochloride, a benzothiazepine derivative of the formula (1), is one of the most useful of drugs which have recently been used as vasodilators especially in alleviation of anginal pains caused by angina of effort and old myocardial infarction.

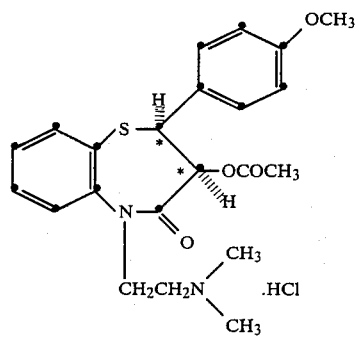

Diltiazem hydrochloride, theoretically, is one of four optical isomers, since it has two asymmetric carbons in its molecule as seen from the above formula (1). Diltiazem hydrochloride commonly named, the most useful isomer of the four, has the (2S,3S) configuration at the asymmetric centers. In the nonstereospecific synthesis, the desired (2S,3S) isomer can be obtained at most in 25% yield. According to the known processes for production of diltiazem, the configuration corresponding to the 2 and 3 positions of diltiazem has successfully be fixed to be cis at the stage of intermediates, which however are still racemates, optically inactive, and need optical resolution with an expensive compound cinchonidine (Jap. Pat. Pub. No. 49-36221). Therefore, the optical resolution in the known process for production of diltiazem decreases the yield to 50% or below, theoretically.

Sharpless et al. described the substantial method for asymmetric epoxidation of allylic alcohols in J. Am. Chem. Soc. 102, 5974–5976 (1980), which is employed in this invention at the early stage of the process.

SUMMARY OF THE INVENTION

The present invention provides a new route to diltiazem hydrochloride of the formula (1), which consists of 10 steps and in which the starting cinnamyl alcohols are epoxidized by the special asymmetric synthesis followed by a series of stereospecific reactions. No optical resolution is required at any stage of the route. The invention also provides two key intermediates used in this route.

DESCRIPTION OF THE PREFERRED EMBODIMENTS

The present invention provides a process for production of diltiazem hydrochloride of the formula:

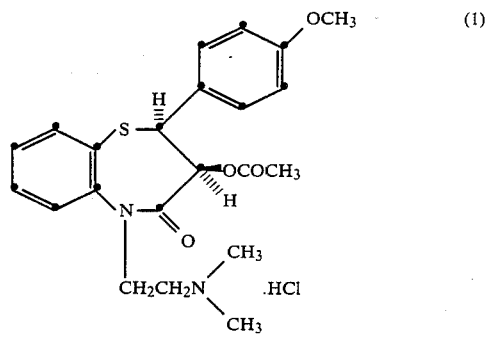

which comprises asymmetrical epoxidation of cinnamyl alcohol of the formula (2):

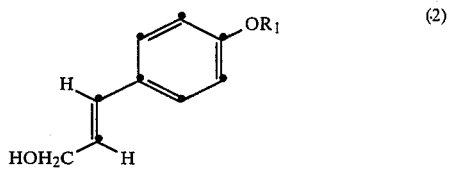

(wherein $R_1$ is acyl)

into an optically active epoxy alcohol (1st step) having the absolute configuration of the formula (3):

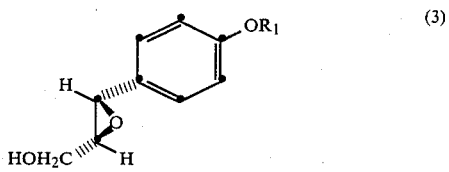

(wherein $R_1$ has the same meaning as defined above), oxidizing said epoxy alcohol (3) to the corresponding carboxylic acid, esterifying the latter to a carboxylic ester (2nd step) of the formula (4):

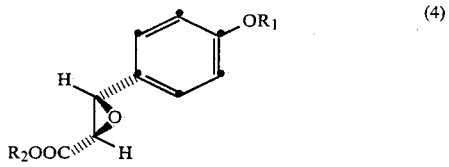

(wherein $R_1$ has the same meaning as defined above and $R_2$ is a lower alkyl), subjecting the latter (4) to hydrogen chloride addition to give a chlorohydrin (3rd step) having the absolute configuration of the formula (5):

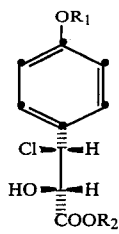

(wherein $R_1$ and $R_2$ each has the same meaning as defined above), reacting the latter (5) with o-nitrothiophenol to give a thioether (4th step) of the formula (6):

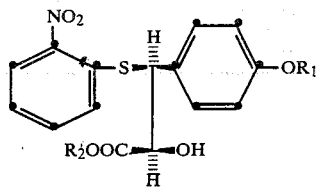

(wherein $R_1$ and $R_2$ each has the same meaning as defined above), subjecting the latter (6) to hydroxy protection to give a hydroxy-protected derivative (5th step) of the formula (7):

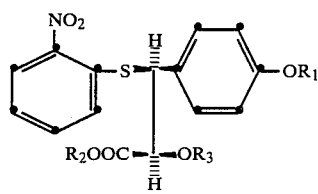

(wherein $R_1$ and $R_2$ each has the same meaning as defined above and $R_3$ is alkoxymethyl, tetrahydrofuranyl, tetrahydropyranyl or benzyl), deacylating and then methylating the latter (7) into a methoxy derivative (6th step) of the formula (8):

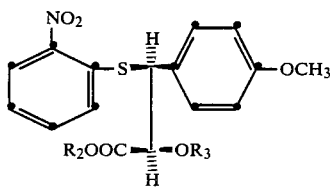

(wherein $R_2$ and $R_3$ each has the same meaning as defined above), reducing the latter (8) into an aminophenylthio derivative (7th step) of the formula (9):

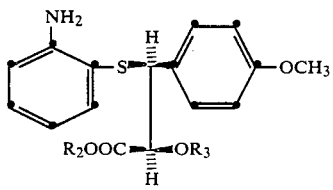

(wherein $R_2$ and $R_3$ each has the same meaning as defined above), cyclizing the latter (9) to give a benzothiazepine derivative (8th step) of the formula (10):

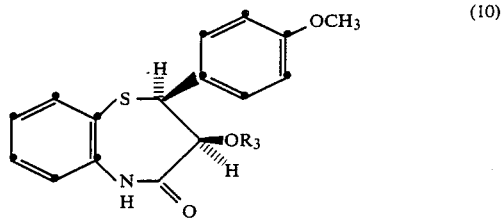

(wherein $R_3$ has the same meaning as defined above), reacting the latter (10) with a 2-(dimethylamino)ethyl halide to give an N-dimethylaminoethyl derivative (9th step) of the formula (11):

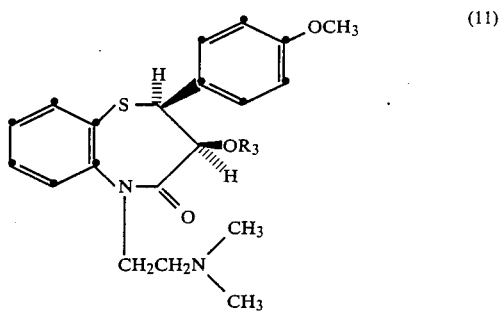

(wherein $R_3$ has the same meaning as defined above), and then acetylating the final intermediate (11) in the presence of an acid catalyst under an anhydrous condition, if required followed by treatment with hydrogen chloride (10th step); and intermediates thereof.

In the aforementioned reaction process, the acyl represented by $R_1$ is $C_2$–$C_6$ acyl derived from fatty acids or acyl having an aromatic ring, including acetyl, propionyl, butylyl, valeryl, hexanoyl, benzoyl and the like. The lower alkyl represented by $R_2$ is $C_1$–$C_6$ alkyl including methyl, ethyl, propyl, isopropyl, butyl, sec-butyl, pentyl, hexyl and the like. Alkoxymethyl represented by $R_3$ is $C_1$–$C_6$ alkyl-substituted alkoxymethyl including methoxymethyl, ethoxymethyl, propoxymethyl, butoxymethyl, pentyloxymethyl, hexyloxymethyl and the like. Each step in the process of the present invention is explained in more detail as follows.

The 1st Step

In this step, the starting trans-cinnamyl alcohols (2) are stereospecifically epoxidized into optically active epoxy alcohols (3), i.e., (2S,3S)-2,3-epoxy-3-(4-acyloxyphenyl)propanols. This reaction is effected by asymmetric epoxidation of the double bond, in which L-(+)-diethyl tartrate is employed as asymmetric inducer (aforementioned method by Sharpless et al.). The epoxidation is achieved by treatment with peroxide such as t-butylperoxide [t-BuOOH] or cumenehydroperoxide in the presence of said asymmetric inducer and titanium tetraisopropoxide[Ti(OiPr)$_4$]. As reaction solvents, halogenated hydrocarbon-type solvents such as methylene chloride and carbon tetrachloride are employed.

The reaction is effected at a low temperature of −10° C. to −30° C. for a period of several hours to several ten hours. Since in this reaction optically active intermediates (3) having the configuration corresponding to the asymmetric centers of diltiazem can be obtained in good yield, no optical resolution nor asymmetric induction is required in any stage of the subsequent reactions. When the substitution on the phenyl is an alkoxy such as methoxy in place of acyloxy ($OR_1$), the epoxidation does not proceed so well because the benzylic position is activated.

The starting material (2) used in this procedure can readily be prepared in the following manner: 4-hydroxycinnamaldehyde or cinnamic acid [I. A. Pearl & S. F. Darling, J. Org. Chem. 22, 1226, (1957)] is respectively acylated into 4-acyloxy-cinnamaldehyde or cinnamic acid, of which the formyl or carboxy (—COOH) is then reduced.

The 2nd Step

In this step, the hydroxymethyl (—$CH_2OH$) of the epoxy alcohols (3) is oxidized into the carboxy, which is then esterified to give the carboxylic acid esters (4). The oxidation in this step can be carried out according to a conventional manner for oxidation of usual primary alcohols into carboxylic acids, and particularly in this invention, oxidation with ruthenium tetraoxide or analogous reagents is preferred in consideration of the other reactive functions such as epoxy, acyl and the like. For example, the reaction is carried out in a two phase system of water and carbon tetrachloride as a solvent, using sodium or potassium salts of metaperiodate or perchlorate ($NaIO_4$, $NaClO_4$, $KIO_4$, $KClO_4$) as an oxygen source in the presence of a catalytic amount of ruthenium compounds (e.g., ruthenium dioxide, ruthenium tetraoxide, ruthenium trioxide) and additionally, an adequate amount of acetonitrile to keep said ruthenium compounds active. The reaction is preferably carried out in a weakly acidic or neutral condition (more preferably, at pH 6–6.5), and in the course of the reaction, a suitable amount of sodium hydrogencarbonate or hydrochloric acid is added in order to adjust the pH range. The reaction is carried out for a period of about 12 hours to about 5 days.

The carboxylic acids (4) ($R_2$=H) obtained through the above oxidation is then esterified in a conventional manner. The esterification may be achieved, for example, with diazoalkanes (diazomethane, diazoethane and the like) or with dialkyl sulfates (dimethyl sulfate, diethyl sulfate and the like).

The 3rd Step

In this step, the carboxylic acid esters (4) obtained in the above step is subjected to hydrogen chloride addition reaction to give the chlorohydrins (5), i.e., 2(s)-hydroxy-3(R)-(4-acyloxyphenyl)-3-chloropropionic acid esters. In this reaction, hydrogen chloride adds to the epoxide sites of the carboxylic acids (4) to cleave the epoxide ring to give chlorohydrins (5). In the reaction of the present invention, addition of hydrogen chloride is effected preferably in polar solvent such as acetonitrile by use of pyridine hydrochloride so as to give the chlorohydrins having the desired configuration. The chlorohydrins (5) are accompanied with a small amount of (2S,3S) isomers as by-products in this step; the former may be applied to the following reaction after purification or directly as a mixture of them.

The 4th Step

In this step, the chlorohydrin (5) obtained in the above step is allowed to react with o-nitrothiophenol to give 2(S)-hydroxy-3(S)-(4-acyloxyphenyl)-3-(2-nitrophenylthio)propionic acids (6). The reaction of this step, which is a substitution reaction of chlorine at the 3-position of the chlorohydrins (5) with the thiophenol, mainly gives 3(S)-isomers with inversion of the configuration at 3-position. The reaction is usually carried out at room temperature in the presence of a suitable base (e.g., triethylamine, pyridine, dimethylaniline, sodium carbonate, potassium carbonate) in a polar solvent such as methanol, ethanol, acetonitrile, dimethylformamide, dimethyl sulfoxide and the like. The reaction usually terminates within a period of 1–5 days, which can be shortened by heating, if desired. The nitrophenylthio-substituted compounds (6) obtained in such a manner has the same (2S,3S)-configuration as that of diltiazem at the two asymmetric centers.

The 5th Step

In this step, the nitrophenylthio-substituted compounds (6) obtained in the above step are protected at the hydroxy by a suitable ether-type protecting group to give the hydroxy protected derivatives (7). Ether type protecting groups to be applied are alkoxymethyl, tetrahydrofuranyl, tetrahydropyranyl, benzyl and the like; the reaction is carried out according to the conventional methods for introduction of protecting groups, for example, using methoxymethyl chloride/pyridine, methylal/phosphorous pentoxide/chloroform, tetrahydrofuran/sulfuryl chloride, dihydropyran/toluenesulfonic acid/dichloromethane, benzyl halide (chloride or bromide)/silver oxide/dimethylformamide and the like.

The 6th Step

In this step, the hydroxy protected derivatives (7) are subjected to reaction for removal of the acyl group $R_1$ to give the free phenols, to which methyl is then introduced to yield the methoxy derivatives (8). Conventional alkali hydrolysis of esters is not usually employed for removal of acyl $R_1$ in the present invention in consideration of influence on the other carboxylic acid ester group —$COOR_2$. In the present invention, it is appropriate to employ an exchange reaction with benzylamine. The reaction is accomplished by addition of an excess amount of benzylamine to the compounds (7) in ether-type solvents such as diethyl ether, tetrahydrofuran, dioxane, glyme and the like and maintenance of the mixture at room temperature for several hours (1–10 hours).

The subsequent methylation of the free phenols can be effected according to usual procedures for methylation of phenols, for example, such as methylation with dimethyl sulfate or with diazomethane.

The 7th Step

In this step, the methoxy derivative (8) is reduced at the nitro of the nitrophenylthio group to give aminophenylthio derivatives (9). The reduction can be accomplished by conventional methods for reduction of nitro compounds into the corresponding amino, for example, hydrogenation in the presence of a suitable catalyst (platinum, palladium, nickel and the like catalyst); reduction with metals, such as iron, tin, titanium and the like, or their lower valent metallic salts [e.g., ferrous chloride ($FeCl_2$), ferrous sulfate ($FeSO_4$), stannous chloride (SnCl$_2$), stannous oxide (SnO), titanium trichloride (TiCl$_3$)] in the presence of weak acids or weak bases. Under the reaction conditions as described in the Examples of this invention, the reaction is carried out with refluxing in a ferrous sulfate.heptahydrate/ammonium hydroxide or triethylamine solution to give the objective aminophenylthio derivatives in high yield.

The 8th Step

In this step, the aminophenylthio derivatives (8) are hydrolyzed the ester R$_2$ to give the free carboxylic acids, which are then cyclized into benzothiazepine derivatives (10).

The alkyl R$_2$ may be removed according to conventional alkali hydrolysis, particularly in this invention, the hydrolysis is preferably carried out in a two-phase system consisting of a solvent (e.g., acetone, tetrahydrofuran, dioxane, glyme) and water saturated with sodium chloride in the presence of an excess amount of a base (e.g., sodium hydroxide, potassium hydroxide) at room temperature with stirring for several hours (1-30 hours).

The subsequent cyclization is preferably carried out according to usual methods for formation of acid amide, such as methods using acid halides (chloride, bromide, etc.), methods using mixed acid anhydrides with a formic acid ester or the carbodiimide method using DCC (dicyclohexylcarbodiimide) as dehydrating agents. More particularly, there is exemplified the reaction with a ethyl halogenoformate (ethyl chloroformate, etc.) and a suitable organic base (triethylamine, pyridine, etc.) in tetrahydrofuran as the mixed acid anhydride method, or the reaction with DCC and 1-hydroxybenztriazole in tetrahydrofuran as the carbodiimide method in these reactions ether-type solvents such as diethyl ether, dioxane and glyme, or benzene-type ones such as benzene and xylene may be employed as well as tetrahydrofuran as mentioned above. In taking the consequent yield and economization into account, the cyclization is preferably carried out with ethyl chloroformate and triethylamine in tetrahydrofuran usually at a temperature of 0°-40° C. for a period of 5 minutes-2 hours, more preferably under stirring at room temperature for 1 hour. Alternatively, the cyclization may also be accomplished under reflux with heating in a suitable solvent (xylene, tetrahydrofuran, etc.).

The 9th Step

In this step, the benzothiazepine derivatives (10) obtained in the above step are subjected to N-alkylation reaction with a 2-(dimethylamino)-ethyl halide to give the N-dimethylaminoethyl derivatives (11); the reaction may be carried out according to a usual manner for alkylation, for example, the benzothiazepine derivatives (10) are converted into appropriate alkali metal salts, which may be subjected to the N-alkylation reaction. More particularly, the benzothiazepine derivatives (10) are allowed to react with a strong base such as lithium hydride, sodium hydride, potassium hydride, sodium amide, butyllithium and the like, dissolved in an appropriate solvent (e.g., dimethylformamide, dimethylsulfoxide, hexamethylphosphamide) to give the corresponding alkali metal salts, which are then allowed to react with a 2-(dimethylamino)ethyl halide (e.g., chloride, bromide). In the reaction, the presence of an adequate amount of silica gel greatly increases the yield. In this step, the reaction is carried out at a temperature of 30°-100° C., preferably, 45°-75° C., for a period of 5-30 hours.

Alternatively, the reaction of the compounds (10) with 2-(dimethylamino)ethyl chloride hydrochloride may also be carried out in the presence of potassium carbonate in ethyl acetate containing a small amount of water (about 3%), whereby the desirable products (11) can be obtained in an excellent yield.

The 10th Step

In this step, the N-dimethylaminoethyl derivatives (11) obtained in the above step are acetylated in the presence of acid catalysts under an anhydrous condition into diltiazem, wherein the acetylation is achieved by an exchange reaction in which the ether-type protecting group R$_3$ is substituted with acetyl. The reaction is carried out by treatment with an equimolar or excess amount of acetylating agents (e.g., acetyl halides such as acetyl chloride and the like) in the presence of Lewis acids (aluminum chloride, titanium tetrachloride, tin chloride, antimony chloride), particularly in the presence of titanium tetrachloride in a solvent such as halogenohydrocarbons (e.g., methylene chloride, chloroform) under an anhydrous condition. After termination of the acetyl exchange reaction in the presence of Lewis acids, if desired, the products may be treated with hydrogen chloride to give diltiazem hydrochloride (1). As mentioned above, the process in the present invention requires no optical resolution procedure in any stage in the whole step for producing diltiazem hydrochloride; therefore, diltiazem hydrochloride can be produced in higher yield than in the prior art methods, and relatively low cost reagents are employed throughout the whole process in the present invention, while expensive reagents such as cinchonidine are required in the prior art methods for optical resolution. As mentioned above, the present invention provides a novel and industrially applicable useful process.

In this process, the compounds of formulae (3) and (4) are novel and can be represented by the formula:

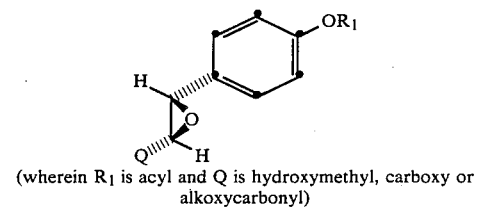

(wherein R$_1$ is acyl and Q is hydroxymethyl, carboxy or alkoxycarbonyl)

The compounds of the formula (6) are also novel. They are very useful intermediates for the stereospecific synthesis in the present invention.

The followings are the representatives of the compounds (3), (4) and (6) of this invention.

Compounds (3) and (4):
(2S,3S)-2,3-epoxy-3-(4-acetoxyphenyl)propanol,
(2S,3S)-2,3-epoxy-3-(4-propionyloxyphenyl)propanol,
(2S,3S)-2,3-epoxy-3-(4-butyryloxyphenyl)propanol,
(2S,3S)-2,3-epoxy-3-(4-benzoyloxyphenyl)propanol,
(2S,3S)-2,3-epoxy-3-[4-(4-nitrobenzoyloxy)phenyl]-propanol,
(2R,3S)-2,3-epoxy-3-(4-acetoxyphenyl)propionic acid,
(2R,3S)-2,3-epoxy-3-(4-propionyloxyphenyl)propionic acid,
(2R,3S)-2,3-epoxy-3-(4-butyryloxyphenyl)propionic acid, (2R,3S)-2,3-epoxy-3-(4-benzoyloxyphenyl)propionic acid,
(2R,3S)-2,3-epoxy-3-[4-(4-nitrobenzoyloxy)phenyl]propionic acid,
methyl (2R,3S)-2,3-epoxy-3-(4-acetoxyphenyl)propionate,
methyl (2R,3S)-2,3-epoxy-3-(4-propionyloxyphenyl)propionate,
methyl (2R,3S)-2,3-epoxy-3-(4-butyryloxyphenyl)propionate,
methyl (2R,3S)-2,3-epoxy-3-(4-benzoyloxyphenyl)propionate,
methyl (2R,3S)-2,3-epoxy-3-[4-(4-nitrobenzoyloxy)phenyl]propionate,
ethyl (2R,3S)-2,3-epoxy-3-(4-acetoxyphenyl)propionate,
ethyl (2R,3S)-2,3-epoxy-3-(4-propionyloxyphenyl)propionate,
ethyl (2R,3S)-2,3-epoxy-3-(4-butyryloxyphenyl)propionate,
ethyl (2R,3S)-2,3-epoxy-3-(4-benzoyloxyphenyl)propionate,
ethyl (2R,3S)-2,3-epoxy-3-[4-(4-nitrobenzoyloxy)phenyl]propionate,
propyl (2R,3S)-2,3-epoxy-3-(4-acetoxyphenyl)propionate,
propyl (2R,3S)-2,3-epoxy-3-(4-propionyloxyphenyl)propionate,
propyl (2R,3S)-2,3-epoxy-3-(4-butyryloxyphenyl)propionate,
propyl (2R,3S)-2,3-epoxy-3-(4-benzoyloxyphenyl)propionate,
propyl (2R,3S)-2,3-epoxy-3-[4-(4-nitrobenzoyloxy)phenyl]propionate.

Compound (6):
2(S)-hydroxy-3(S)-(4-formyloxyphenyl)-3-(2-nitrophenylthio)propionic acid,
2(S)-hydroxy-3(S)-(4-acetoxyphenyl)-3-(2-nitrophenylthio)propionic acid,
2(S)-hydroxy-3(S)-(4-propionyloxyphenyl)-3-(2-nitrophenylthio)propionic acid,
2(S)-hydroxy-3(S)-(4-butyryloxyphenyl)-3-(2-nitrophenylthio)propionic acid,
2(S)-hydroxy-3(S)-(4-benzoyloxyphenyl)-3-(2-nitrophenylthio)propionic acid,
2(S)-hydroxy-3(S)-[4-(4-nitrobenzoyloxy)phenyl]-3-(2-nitrophenylthio)propionic acid,
methyl 2(S)-hydroxy-3(S)-(4-formyloxyphenyl)-3-(2-nitrophenylthio)propionate,
methyl 2(S)-hydroxy-3(S)-(4-acetoxyphenyl)-3-(2-nitrophenylthio)propionate,
methyl 2(S)-hydroxy-3(S)-(4-propionyloxyphenyl)-3-(2-nitrophenylthio)propionate,
methyl 2(S)-hydroxy-3(S)-(4-butyryloxyphenyl)-3-(2-nitrophenylthio)propionate,
methyl 2(S)-hydroxy-3(S)-(4-benzoyloxyphenyl)-3-(2-nitrophenylthio)propionate,
methyl 2(S)-hydroxy-3(S)-[4-(4-nitrobenzoyloxy)phenyl]-3-(2-nitrophenylthio)propionate,
ethyl 2(S)-hydroxy-3(S)-(4-formyloxyphenyl)-3-(2-nitrophenylthio)propionate,
ethyl 2(S)-hydroxy-3(S)-(4-acetoxyphenyl)-3-(2-nitrophenyl)propionate,
ethyl 2(S)-hydroxy-3(S)-(4-propionyloxyphenyl)-3-(2-nitrophenylthio)propionate,
ethyl 2(S)-hydroxy-3(S)-(4-butyryloxyphenyl)-3-(2-nitrophenylthio)propionate,
ethyl 2(S)-hydroxy-3(S)-(4-benzoyloxyphenyl)-3-(2-nitrophenylthio)propionate,
ethyl 2(S)-hydroxy-3(S)-[4-(4-nitrobenzoyloxy)phenyl]-3-(2-nitrophenylthio)propionate,
propyl 2(S)-hydroxy-3(S)-(4-formyloxyphenyl)-3-(2-nitrophenylthio)propionate,
propyl 2(S)-hydroxy-3(S)-(4-acetoxyphenyl)-3-(2-nitrophenylthio)propionate,
propyl 2(S)-hydroxy-3(S)-(4-propionyloxyphenyl)-3-(2-nitrophenylthio)propionate,
propyl 2(S)-hydroxy-3(S)-(4-butyryloxyphenyl)-3-(2-nitrophenylthio)propionate,
propyl 2(S)-hydroxy-3(S)-(4-benzoyloxyphenyl)-3-(2-nitrophenylthio)propionate,
propyl 2(S)-hydroxy-3(S)-[4-(4-nitrobenzoyloxy)phenyl]-3-(2-nitrophenylthio)propionate.

The following sections "Preparation" and "Example" serve to illustrate the practical production and formation of the objective compounds in this invention.

PREPARATION (A) 4-Acetoxy-trans-cinnamic acid:

To a solution of 100.0 g (0.61 mol) of 4-hydroxy-trans-cinnamic acid in 500 ml of pyridine is added 115 ml of acetic anhydride and the solution kept at room temperature for one hour. Water (10.8 ml) is added and the mixture allowed to stand for 10 minutes and concentrated in vacuo. The residue is poured into ice-water (1.5 l) containing 150 ml of concentrated hydrochloric acid. The crystalline compound precipitated is collected by filtration and washed with water. The precipitate is dissolved in 1.2 l of 90% alcohol and the solution refluxed under heating for 15 minutes to decompose anhydride of 4-acetoxy-trans-cinnamic acid formed. Decoloring carbon is added, the mixture filtered while hot, and the filtrate ice-cooled. The precipitated crystals are collected by filtration and washed with 90% alcohol to give 117.5 g of the above-defined compound. Yield 93.3%, mp 212°–213.5° C.

(B) 4-Acetoxy-trans-cinnamyl alcohol (I):

To a cold solution (10° C.) of 10.000 (48.5 mmol) of 4-acetoxy-trans-cinnamic acid in 72 ml of anhydrous dioxane is added 7.44 ml (53.35 mmol) of triethylamine. Ethyl chloroformate (5.08 ml, 53.35 mmol) in anhydrous dioxane (10 ml) is added to the mixture over 15 minutes with stirring. The resulting mixture is stirred for further 30 minutes at 10°–12° C. and then filtered. The filtrate is dropwise added to a suspension of 2.295 g (60.624 mmol) of powdered sodium borohydride in 100 ml of anhydrous dioxane and 1.22 ml of anhydrous dimethylformamide, and the mixture stirred at 8° C. for one hour. Acetone (7 ml) is added, the mixture stirred for 30 minutes, and 3.47 ml of acetic acid added. The mixture is concentrated in vacuo to about 100 g and extracted with benzene and water. The organic layer is washed with chilled 10% aqueous sodium carbonate and water, successively, dried over anhydrous magnesium sulfate, and concentrated in vacuo to give 4-acetoxy-trans-cinnamylalcohol (I). This is recrystallized from carbon tetrachloride to give 6.673 g of colorless prisms, mp.73.5°–75° C. The mother liquor is concentrated in vacuo and 1.622 g of residue is dissolved in water and hexane. The aqueous layer is extracted with benzene and the benzene layer is washed with chilled 10% aqueous sodium carbonate and water twice, dried over anhydrous magnesium sulfate, and concentrated in vacuo to give 4-acetoxy-trans-cinnamylalcohol (I). This is recrystallized from carbon tetrachloride to give 536 mg of colorless prisms, mp. 73°–74.5° C. Total yield 7.209 g (77.3%). A portion of the product is recrystallized from ether/hexane to give an authentic specimen as prisms having mp. 75°–76° C.

EXAMPLE (1) (2S,3S)-2,3-epoxy-3-(4-acetoxyphenyl)propanol (II):

To an ice-cooled solution of 384 Mg (2 mmol) of 4-acetoxy-trans-cinnamylalcohol (I) in 18 ml of anhydrous methylene chloride is added 1.2 ml of 3.32N-cumene hydroperoxide/methylene chloride solution under nitrogen atmosphere and the reaction mixture stirred under ice-cooling. 0.402N Solution (0.666 ml) of titanium tetraisopropoxide in methylene chloride is mixed with 0.407N solution (0.98 ml) of diethyl-L-(+)-tartrate in methylene chloride under nitrogen atmosphere, and the mixture allowed to stand for one hour and then added to the above reaction mixture in three portions every 10 minutes. After 45 minutes, the mixture is poured into a saturated aqueous solution of sodium fluoride (2.5 g) with vigorous stirring at room temperature for 15 minutes. Sodium chloride (16 g) is added and the mixture stirred for further 15 minutes. The precipitated gelatinous material is collected by filtration through a filter aid and washed with methylene chloride. The organic layer is dried over anhydrous magnesium sulfate and concentrated in vacuo. 1.24 g Oily residue is dissolved in carbon tetrachloride and filtered. The filtrate is concentrated in vacuo and a residue is dissolved in 5 ml of benzene, chromatographed on silica gel (Lobor B; made by Merck) and eluted with ethyl acetate/hexane (1:1) (each fraction 11 ml). Fractions which show a single spot in thin layer chromatography are collected and concentrated in vacuo to give 309 mg (74.3%) of the above-defined compound (II) as crystalline, mp. 59°–61° C., $[\alpha]_D^{23}$: −23.7±0.6° (c 1.017, chloroform).

This is recrystallized from ether to give colorless needles, mp. 59.5°–60.5° C., $[\alpha]_D^{24.5}$: −23.5±1.2° (c 0.514, chloroform). Anal. Calcd. for $C_{11}H_{12}O_4$: C;63.45, H;5.81, Found: C; 63.35, H; 5.68. IR Spectrum: νmax (Nujol) 3240, 1755, 1608, 1594, 1510 cm$^{-1}$.

NMR Spectrum (CDCl$_3$: CD$_3$OD=9:1 ppm): 7.3(d, J=9 Hz, 2H), 7.05(d,J=9 Hz,2H), 3.95(q,J=3 Hz, J=13.5 Hz, 1H), 3.88(d,J=3 Hz, 1H), 3.72(q,J=4.5 Hz,J=13.5 Hz,1H), 3.18(m, 1H), 2.27(s,3H).

(2) (2R,3S)-2,3-epoxy-3-(4-acetoxyphenyl)propionic acid (III) and methyl (2R,3S)-2,3-epoxy-3-(4-acetoxyphenyl)propionate (IV):

To a solution of 20.112 g (94.03 mmol) of sodium metaperiodide in 273 ml of water is added 5.321 g (63.34 mmol) of sodium hydrogencarbonate in small portions with stirring, whereby white salt is precipitated. Acetonitrile (182 ml) and carbon tetrachloride (182 ml) are added to the reaction mixture with stirring. Then 91 mg (0.684 mmol) of ruthenium dioxide and 6.528 g (31.35 mmol) of (2S,3S)-2,3-epoxy-3-(4-acetoxyphenyl)-propanol (II) are added at 2°–3° C. Further 13.41 g (62.7 mmol) of sodium metaperiodate and 169 mg of ruthenium dioxide are added to the mixture. The mixture is maintained at pH 6–6.5 by addition of sodium hydrogencarbonate or 1.2N hydrochloric acid and then allowed to stand for 20 hours. After 43 hours from the beginning of the reaction, 19.5 ml of isopropanol is added, and the mixture stirred for 20 minutes, the precipitate removed by filtration and washed with water and chloroform. The filtrate and the washings are combined and the aqueous layer is extracted with chloroform. The aqueous layer is adjusted at pH 1 by portionwise addition of 17.0 g (0.135 mmol) of oxalic acid and extracted with three 120 ml portions of chloroform. The chloroform layer is washed with a chilled aqueous sodium chloride, dried over magnesium sulfate. Triethylamine (4.4 ml) is added, and the solution evaporated in vacuo. The mixture of 10.44 g (124.27 mmol) of powdered sodium hydrogencarbonate in 64 ml of dimethyl formamide is added to the oily residue (12.05 g), stirred for an hour, then 5.5 ml (58.1 mmol) of dimethyl sulfate is added, and the mixture allowed to stand for 2 hours. The reaction mixture is poured into 640 ml of ice water, and seed crystals are added and stirred. The crystalline precipitate is collected by filtration and washed with water. The filtrate is extracted with ethyl acetate and the ethyl acetate solution is washed with water, dried over anhydrous magnesium sulfate, and concentrated in vacuo. The combined crystals and residue are recrystallized from ether/hexane to give 4.509 g of methyl (2R,3S)-2,3-epoxy-3-(4-acetoxyphenyl)propionate (IV) as colorless needles, mp. 67.5°–68° C., $[\alpha]_D^{24}$: −138.4±1.6° (c 1.130, chloroform). A portion of the compound is further recrystallized from the same solvent system to give pure sample showing mp. 67°–68° C., $[\alpha]_D^{23.5}$: −140.7±1.8° (c 1.008, chloroform). Anal. Calcd. for $C_{12}H_{12}O_5$: C;61.01, H;5.12, Found: C;60.74, H;5.18. IR Spectrum: νmax(Nujol): 1760, 1730, 1610, 1599 cm$^{-1}$. NMR Spectrum (CDCl$_3$, ppm): 7.35(d, J=9 Hz, 2H), 7.08(d, J=9 Hz, 2H), 4.10(d, J=2 Hz, 1H), 3.83(s, 3H), 3.48(d,J=2 Hz, 1H), 2.30(s,3H).

The mother liquor of the recrystallization is worked up again to give 410 mg of the above-defined compound (IV) as crystalline, mp. 66°–67.5° C. The mother liquors (1.228 g) is subjected to liquid chromatography on two columns of Lobor B with benzene:acetone (30:1) as an eluent. The main fractions are collected and recrystallized from ether/hexane to give 709 mg of the title compound (IV), mp. 67.5°–68° C., $[\alpha]_D^{25}$: −137.5±1.6° (c 1.104, chloroform). Total yield of the title compound (IV) is 5.628 g (75.9%).

(3) Methyl 2(S)-hydroxy-3(R)-(4-acetoxyphenyl)-3-chloropropionate (V):

A solution of 1.550 g (13.4 mmol) of pyridine hydrochloride and 1.056 g (4.47 mmol) of methyl (2R,3S)-2,3-epoxy-3-(4-acetoxyphenyl)-propionate (IV) dissolved in 19.5 ml of acetonitrile is allowed to stand at room temperature for 6 hours under nitrogen atmosphere. 0.604 ml Of 2.1N hydrogen chloride/acetonitrile solution is added, the mixture allowed to stand at room temperature for 3 days, and then 1.1 ml, 0.425 ml and 0.425 ml of 2.1N hydrogen chloride/acetonitrile solution are added in order every 2 hours.

After 2 hours, the reaction mixture is poured into ice-water and extracted with chloroform. The chloroform layer is successively washed with diluted hydrochloric acid, ice-water, sodium hydrogencarbonate and ice-water, dried over anhydrous magnesium sulfate and evaporated in vacuo to give 1.267 g of a mixture of the chlorides (V) and (V′) as crystalline. The mixture is used in the following step without purification.

(4) Methyl 2(S)-hydroxy-3(S)-(4-acetoxyphenyl)-3-(2-nitrophenylthio)propionate (VI):

A solution of 1.267 g (4.47 mmol) of the mixture of chlorides (V) and (V′) obtained in the above step, 1.040 g (6.7 mmol, 1.5 eq) of o-nitrothiophenol and 0.623 ml (4.47 mmol, 1 eq) of triethylamine dissolved in 2.21 ml of acetonitrile is allowed to stand at room temperature for 3 days in argon atmosphere, poured into 50 ml of ice-water, and extracted with chloroform. The organic layer is washed with cold diluted hydrochloric acid, water, sodium hydrogen-carbonate, and water, successively, dried over anhydrous magnesium sulfate, and evaporated in vacuo. The yellow residue (2.40 g) obtained is treated with 15 ml of ethanol, the remaining insoluble material is filtered off. The filtrate is concentrated in vacuo. The residue is dissolved in 6 ml of ethanol, and seed crystals are added to the solution. The crystalline precipitate is collected by filtration to give 1.079 g (55.2%) of the title compound as yellow prisms, which contain one molecule of ethanol, mp. 75°–76° C., $[\alpha]_D^{22.5} + 82.3 \pm 1.2°$ (c 1.010, chloroform).

The mother liquor is worked up in the same manner as mentioned above to give further 66 mg (3.4%) of the title compound, mp. 72.5°–75° C. The mother liquor (649 mg) is subjected to liquid chromatography on two columns of Lobor B (made by Merck) with benzene-:acetone (15:1) as an eluent. The main fractions are collected and concentrated in vacuo. The residue is recrystallized from ethanol to give 42 mg (2.1%) of the title compound as yellow prisms, mp. 75°–76° C., $[\alpha]_D^{23.5} + 82.9 \pm 1.1°$ (c 1.071, chloroform). This is recrystallized from ethanol to give yellow needles, mp. 76° C., $[\alpha]_D^{23} + 84.3 \pm 1.3°$ (c 0.945, chloroform). Anal. Calcd. for $C_{18}H_{17}NO_7S \cdot C_2H_5OH$: C;54.91, H;5.30, N;3.20, S;7.33, Found: C;54.63, H;5.02, N;3.35, S;7.10.

IR Spectrum: $\nu$max(Nujol) 3470, 3240, 1754, 1739, 1719, 1590, 1565, 1512, 1502 cm$^{-1}$. NMR Spectrum ($CD_3COCD_3$: $CD_3OD$, 4:05, ppm): 8.1–7.0(8H), 5.03(d,J=4 Hz,1H), 4.63(d,J=4 Hz, 1H), 3.63(s,3H), 2.23(s,3H), 1.13(t,J=7 Hz, 3H).

Fractions following to the fractions of the title compound (VI) give 146 mg (8.3%) of methyl 2(S)-hydroxy-3(R)-(4-acetoxyphenyl)-3-(2-nitrophenylthio)-propionate (VI') as a by-product. Total yield of the compound (VI) is 1.187 g.

(5) Methyl 2(S)-methoxymethoxy-3(S)-(4-acetoxyphenyl)-3-(2-nitrophenylthio)propionate (VII):

1.044 g (2.39 mmol) of methyl 2(S)-hydroxy-3(S)-(4-acetoxyphenyl)-3-(2-nitrophenylthio)propionate (VI) containing one molecule of ethanol as solvent of crystallization is dissolved in 12 ml of anhydrous chloroform, the chloroform removed by distillation under atmospheric pressure, and the resulting residue dried under reduced pressure. This procedure is repeated once more, and the resulting residue is dissolved in a mixture of 7 ml of anhydrous chloroform and 2.29 ml (26.24 mmol) of methylal. The mixture is added to a suspension of 1.288 g (9.07 mmol) of phosphorus pentoxide in 5 ml of anhydrous chloroform with stirring. The mixture is stirred at room temperature for 2.5 hours, and the supernatant of the reaction mixture is poured into cold sodium hydrogencarbonate solution, and the mixture extracted with chloroform. The chloroform layer is washed with ice-water, dried over anhydrous magnesium sulfate and evaporated in vacuo. The crystalline residue obtained is recrystallized from methanol to give 967 mg (93%) of the title compound as yellow needles, mp. 115°–116.5° C., $[\alpha]_D^{24} + 48.5 \pm 0.9°$ (c 0.985, chloroform). A portion of the compound is further recrystallized from methanol to give a pure specimen having mp. 117°–118.5° C., $[\alpha]_D^{24} + 49.9 \pm 0.9°$ (c 1.018, chloroform). Anal. Calcd. for $C_{20}H_{21}NO_8S$: C;55.17, H;4.86, N;3.21, S;7.36, Found: C;55.02, H;4.86, N;3.27, S;7.28. IR Spectrum: $\nu$max(Nujol) 1740, 1592, 1567, 1512, 1502 cm$^{-1}$. NMR Spectrum ($CDCl_3$ ppm): 8.1–7.0(8H), 4.88(d,J=6 Hz,1H), 4.75(d,J=7 Hz,1H), 4.58(d,J=7 Hz,1H), 4.51(d,J=6 Hz,1H), 3.60(s,3H), 3.13(s,3H), 2.27(s,3H).

(6-a) Methyl 2(S)-methoxymethoxy-3(S)-(4-hydroxyphenyl)-3-(2-nitrophenylthio)propionate (VIII):

To a solution of 7.020 g (16.12 mmol) of methyl 2(S)-methoxymethoxy-3(S)-(4-acetoxyphenyl)-3-(2-nitrophenylthio)propionate (VII) in 120 ml of tetrahydrofuran is added 5.30 ml (48.62 mmol) of benzylamine, and the mixture kept at 30° C. for 2 days. The reaction mixture is then poured into diluted hydrochloric acid and extracted with chloroform. The chloroform layer is washed well with water, dried over anhydrous magnesium sulfate, and evaporated in vacuo to give 9.173 g (quantitative yield) of the title compound containing one molecule of benzylacetamide per molecule as an yellow oil, $[\alpha]_D^{23} + 22.4 \pm 0.6°$ (c 0.978, chloroform).

A portion (1.62 g) of this oil is subjected to liquid chromatography on a column of Lobor B (made by Merck) with benzene:acetone (5:1) as an eluent, and the main fraction are collected to give 1.085 g of the title compound, $[\alpha]_D^{24} + 32.7°$ (c 1.077, chloroform), which does not contain benzylacetamide.

(6-b) Methyl 2(S)-methoxymethoxy-3(S)-(4-methoxyphenyl)-3-(2-nitrophenylthio)propionate (IX):

To a solution of 1.861 g (3.36 mmol) of methyl 2(S)-methoxymethoxy-3(S)-(4-hydroxyphenyl)-3-(2-nitrophenylthio)propionate (VII), which contains one molecule of benzylacetamide, dissolved in 20 ml of methanol is added diazomethane/ether solution, and after 14.5 hours the solvent evaporated in vacuo. Water (16 ml) is added to the resulting oily residue, the mixture rubbing well with a glass rod under warming, then ice-cooled, and the supernatant removed by decantation. This procedure is further twice. The resulting residue is dissolved in 23 ml of alcohol, 10 ml of water added, seed crystals are added, and the mixture allowed to stand at room temperature. In the course of th crystallization, additional 23.1 ml of water is added to complete the crystallization. 1.287 g (94%) Of the title compound is obtained as yellow needles, mp. 57°–60° C. This is recrystallized from aqueous alcohol to give 1.240 g (90.6%) of yellow needles or rods, mp. 64.5–66° C., $[\alpha]_D^{23} + 36.9 \pm 0.8°$ (c 1.000, chloroform). Anal. Calcd. for $C_{19}H_{21}NO_7S$: C;56.01, H;5.20, N;3.44, S;7.87, Found: C;55.87, H;5.17, N;3.64, S;7.99. IR Spectrum: $\nu$max (Nujol) 1754, 1712, 1609, 1592, 1565, 1510 cm$^{-1}$. NMR Spectrum ($CDCl_3$,ppm): 8.1–6.7(8H), 4.82(d,J=6.5 Hz,1H), 4.73(d,J=7 Hz,1H), 4.60(d,J=7 Hz,1H), 4.47(d,J=6.5 Hz,1H), 3.77(s,3H), 3.58(s,3H), 3.18(s,3H).

(7) Methyl 2(S)-methoxymethoxy-3(S)-(4-methoxyphenyl)-3-(2-aminophenylthio)propionate (X):

To a mixture of 18.8 ml (18.8 mmol) of 1N-ammonium hydroxide and 5.219 g (18.8 mmol, 9.2 eq) of ferrous sulfate heptahydrate dissolved in 19.6 ml of water is added a solution of 831 mg (2.04 mmol) of methyl 2(S)-methoxymethoxy-3(S)-(4-methoxyphenyl)-3-(2-nitrophenylthio)propionate (IX) dissolved in 34.2 ml of methanol, and the mixture refluxed. Concentrated ammonium hydroxide is added every five minutes to maintain the mixture alkaline (total volume of ammonium hydroxide is 5.4 ml.). After 2 hours and 20 minutes, the reaction mixture is cooled to room temperature, 25 ml of ethyl acetate is added thereto, the soluble material is filtered off.

The filtrate is extracted with ethyl acetate, the organic layer washed with water, dried over anhydrous magnesium sulfate and evaporated in vacuo to give 749 mg (97.3%) of the title compound as crystalline. $[\alpha]_D^{23.5}+293\pm3.4°$ (c 0.990, chloroform). This is recrystallized from aqueous alcohol to give pure sample, mp. 74.5°–75° C., $[\alpha]_D^{22}+304\pm3.4°$ (c 1.000, chloroform). Anal. Calcd. for $C_{19}H_{23}NO_5S$: C;60.46, H;6.14, N;3.71, S;8.50, Found: C;60.34, H;6.06, N;3.65, S;8.42. IR Spectrum: $\nu$max(Nujol) 3460, 3370, 3360, 1735, 1605, 1515 cm$^{-1}$. NMR Spectrum (CDCl$_3$, ppm): 7.3–6.3(8H), 4.75(d,J=7 Hz,1H), 4.60(d,J=7 Hz,1H), 4.38(s,2H), 3.75(s,3H), 3.52(s,3H), 3.23(s,3H).

(8-a) 2(S)-Methoxymethoxy-3(S)-(4-methoxyphenyl)-3-(2-aminophenylthio)propionic acid (XI):

To a solution of 749 mg (1.98 mmol) of methyl 2(S)-methoxymethoxy-3(S)-(4-methoxyphenyl)-3-(2-aminophenylthio)propionate (X) in 14.4 ml of tetrahydrofuran is added 6.03 ml (7.9 mmol) of 1.3N-sodium hydroxide and the resulting two phase reaction mixture is stirred at room temperature. After the lapse of 19.5 hours, 81 ml (8.1 mmol) of 0.1N-hydrochloric acid is slowly added with stirring under ice-cooling, and the precipitate is collected by filtration, washed with water and dried to give 651 mg (91.4%) of the title compound, mp. 155°–158° C., $[\alpha]_D^{23}+392.3\pm7.5°$ (c 0.574, ethanol). This is recrystallized from aqueous ethanol to give colorless needles, mp. 160.5°–162° C., $[\alpha]_D^{24}+408.7\pm8.9°$ (c 0.507, ethanol). Anal. Calcd. for $C_{18}H_{21}NO_5S$: C;59.49, H;5.82, N;3.85, S;8.82, Found: C;59.30, H;5.81, N;3.86, S;8.63. IR Spectrum: $\nu$max(Nujol) 3458, 3370, 3360, 1732, 1602, 1516 cm$^{-1}$. NMR Spectrum (CDCl$_3$: CD$_3$OD=4.5:1, ppm): 7.3–6.3(8H), 4.75(d,J=7 Hz, 1H), 4.58(d, J=7 Hz, 1H), 4.43(s,2H), 3.73(s,3H), 3.20(s,3H).

(8-b) (2S,3S)-Dihydro-3-methoxymethoxy-2-(4-methoxyphenyl)-1,5-benzothiazepin-4(5H)-one (XII):

To a solution of 50 mg (0.138 mmol) of 2(S)-methoxymethoxy-3(S)-(4-methoxyphenyl)-3-(2-aminophenylthio)propionate (XI) dissolved in 1.73 ml of a triethylamine/tetrahydrofuran mixture (97 mg of triethylamine diluted to 10 ml with tetrahydrofuran) is added 1.58 ml of ethyl chloroformate/tetrahydrofuran solution (a solution of 114 mg of ethyl chloroformate diluted to 10 ml with tetrahydrofuran). After one hour, chloroform is added and the mixture poured into ice-cooled hydrochloric acid, and extracted with chloroform. The chloroform layer is washed with water, aqueous sodium hydrogencarbonate and water successively, dried over anhydrous magnesium sulfate and evaporated in vacuo. The residue (49 mg) is kneaded well with hexane, and the supernatant removed by decantation to give 45 mg (94.7%) of the title compound, mp. 121.5°–124° C., $[\alpha]_D^{23}+69.3\pm2.3°$ (c 0.466, ethanol). This is recrystallized from ethanol to give colorless needles, mp. 125°–125.5° C., $[\alpha]_D^{22}+72.8\pm1.1°$ (c 1.012, ethanol). Anal. Calcd. for $C_{18}H_{19}NO_4S$: C;62.59, H;5.54, N;4.06, S;9.28, Found: C;62.49, H;5.40, N;4.08, S;9.25. IR Spectrum: $\nu$max(Nujol) 3260, 1705, 1608, 1582, 1589, 1510 cm$^{-1}$. NMR Spectrum (CDCl$_3$ ppm): 7.8–6.6(8H), 5.12(d,J=7 Hz,1H), 4.57(d,J=7 Hz, 1H), 4.48(s,2H), 3.72(s,3H), 3.22(s,3H).

(9) (2S,3S)-Dihydro-5-[2-(dimethylamino)ethyl]-3-methoxymethoxy-2-(4-methoxyphenyl)-1,5-benzothiazepin-4(5H)-one (XIII):

To a mixture of 700 mg (2.03 mmol) of (2S,3S)-dihydro-3-methoxymethoxy-2-(4-methoxyphenyl)-1,5-benzothiazepin-4(5H)-one (XII) and 350 mg of silica gel (Wakogel C-200) for chromatography which has been dried under reduced pressure at 50° C. for 10 hours is added 7 ml of anhydrous dimethyl sulfoxide and 124 mg (2.84 mmol, 1.4 eq) of 55% sodium hydride-mineral oil suspension, and the mixture is stirred at room temperature for 30 minutes under argon atmosphere. A solution of 0.315 ml (1.4 eq) of 2-(dimethylamino)ethyl chloride dissolved in 0.425 ml of anhydrous ether is added to the reaction mixture, the resulting mixture stirred in a thermostat kept at 30° C. After 5.5 hours, the reaction mixture is diluted with 10 ml of benzene, and the silica gel filtered off and washed with 15 ml of benzene. The benzene layer is washed with water thrice, dried over anhydrous magnesium sulfate and evaporated in vacuo. The oily residue (938 mg) is dissolved in 20 ml of 90% methanol and the solution washed with 20 ml of n-hexane twice, the hexane layers extracted with two 20 ml portions of 90% methanol, and the methanol layers concentrated in vacuo. Water is added to the residue, and the mixture extracted with chloroform. The organic layer is dried over anhydrous magnesium sulfate and evaporated in vacuo to give 789 mg (93.5%) of the title compound as a colorless oil, $[\alpha]_D^{22.5}+116.9\pm1.6°$ (c 0.986, chloroform).

IR Spectrum: $\nu$max(CHCl$_3$) 1674, 1611, 1585, 1512 cm$^{-1}$.

NMR Spectrum (CDCl$_3$, ppm): 7.8–6.8(8H), 4.97(d,J=7.5 Hz,1H), 4.47(s,2H),4.37(d,J=7.5 Hz,1H), 3.80(s,3H), 3.22(s,3H), 2.27(s,6H).

(10) 5-[2-Dimethylamino)ethyl]-2,3-dihydro-3(S)-hydroxy-2(S)-(4-methoxyphenyl)-1,5-benzothiazepin-4(5H)-one.acetate hydrochloride [Diltiazem hydrochloride]:

A solution of 144 mg (0.346 mmol) of (2S,3S)-dihydro-5-[2-dimethylamino)ethyl]-3-methoxymethoxy-2-(4-methoxyphenyl)-1,5-benzothiazepin-4(5H)-one (XIII) dissolved in 6.05 ml of anhydrous methylene chloride under nitrogen atmosphere is dropwise added to a mixture of 1.54 ml (0.38 mmol) of 0.248N-titanium tetrachloride/methylene chloride and 1.07 ml (1.04 mmol) of 0.973N-acetyl chloride/methylene chloride solution with stirring over a period of 10 minutes. After 3 hours and 40 minutes, the reaction mixture is poured into ice-water containing sodium hydrogencarbonate. The insoluble material is removed by filtration with aid of celite, and washed with chloroform. The combined filtrate and washings are extracted with chloroform, and the organic layer washed with two portions of water, dried over anhydrous magnesium sulfate and evaporated in vacuo. Ether (9 ml) is added to 132 mg of the crystalline residue, and the insoluble material removed; the ether layer is decolored with active carbon, and evaporated in vacuo. 123.5 mg Of the colorless crystalline residue is dissolved in 14 ml of isopropyl ether, and 0.69 ml of a 0.473N-hydrogen chloride/methanol solution is added. Crystalline precipitate, which appeared is collected by filtration, and washed with isopropyl ether to give 130.6 mg (83.7%) of the title compound as colorless fine needles, mp. 207°–210.5° C., $[\alpha]_D^{24}+98.0\pm1.4°$ (c 0.970, methanol). This is recrystallized from ethanol/isopropanol to give 114 mg (73.1%) of colorless fine needles, mp. 207.5°–212° C., $[\alpha]_D^{24}+98.3\pm1.4°$ (c 1.002, methanol). This product is identical with an authentic specimen of diltiazem hydrochloride synthesized in the prior art in their physical constants.

What is claimed is:

1. A process for production of diltiazem hydrochloride of the formula (1):

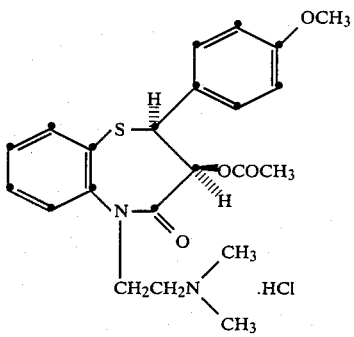 (1)

which comprises asymmetrical epoxidation of cinnamyl alcohol of the formula (2):

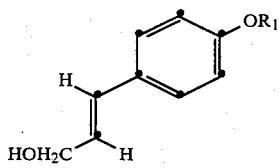 (2)

wherein $R_1$ is acyl into an optically active epoxy alcohol having the absolute configuration of the formula (3):

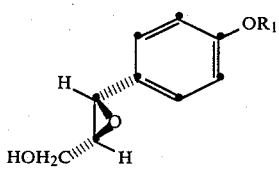 (3)

wherein $R_1$ has the same meaning as defined above, oxidizing said epoxy alcohol (3) to the corresponding carboxylic acid, esterifying the latter to a carboxylic ester of the formula (4):

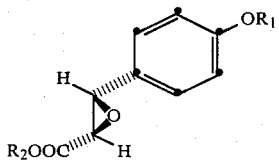 (4)

wherein $R_1$ has the same meaning as defined above and $R_2$ is a lower alkyl, subjecting the latter (4) to hydrogen chloride addition to give a chlorohydrin having the absolute configuration of the formula (5):

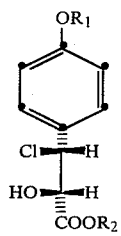 (5)

wherein $R_1$ and $R_2$ each has the same meaning as defined above, reacting the latter (5) with o-nitrothiophenol to give a thioether of the formula (6):

(6)

wherein $R_1$ and $R_2$ each has the same meaning as defined above,
wherein $R_1$ and $R_2$ each has the same meaning as defined above, subjecting the latter (6) to hydroxy protection to give a hydroxy-protected derivative of the formula (7):

(7)

wherein $R_1$ and $R_2$ each has the same meaning as defined above and $R_3$ is alkoxymethyl, tetrahydrofuranyl, tetrahydropyranyl or benzyl, deacylating and then methylating the latter (7) into a methoxy derivative of the formula (8):

(8)

wherein $R_2$ and $R_3$ each has the same meaning as defined above, reducing the latter (8) into an aminophenylthio derivative of the formula (9):

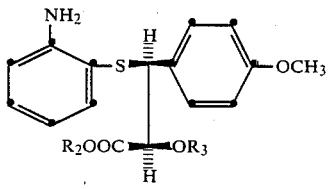 (9)

-continued
wherein R₂ and R₃ each has the same meaning as defined above, cyclizing the latter (9) to give a benzothiazepine derivative of the formula (10):

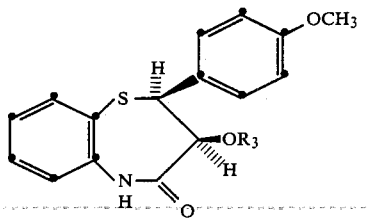

wherein R₃ has the same meaning as defined above, to give an N-dimethylaminoethyl derivative of the formula (11):

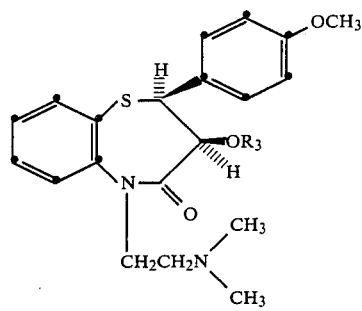

wherein R₃ has the same meaning as defined above, and then acetylating the final intermediate (11) in the presence of an acid catalyst under an anhydrous condition, if required followed by treatment with hydrogen chloride.

* * * * *